(12) United States Patent
Agyemang et al.

(10) Patent No.: US 9,179,701 B2
(45) Date of Patent: Nov. 10, 2015

(54) 2-MERCAPTO-5-METHYL-4-HEPTANONE AND ITS USE IN FLAVOR AND FRAGRANCE COMPOSITIONS

(71) Applicant: International Flavors & Fragrances Inc., New York, NY (US)

(72) Inventors: David O. Agyemang, East Brunswick, NJ (US); Kathryn A. Bardsley, Howell, NJ (US); Zhen Chen, Aberdeen, NJ (US); Adam Jan Janczuk, Parlin, NJ (US); Laurence Trinnaman, Montvale, NJ (US)

(73) Assignee: International Flavors & Fragrances, Inc., New York, NY (US)

( * ) Notice: Subject to any disclaimer, the term of this patent is extended or adjusted under 35 U.S.C. 154(b) by 145 days.

(21) Appl. No.: 14/105,364

(22) Filed: Dec. 13, 2013

(65) Prior Publication Data

US 2014/0171517 A1 Jun. 19, 2014

Related U.S. Application Data

(60) Provisional application No. 61/737,987, filed on Dec. 17, 2012.

(51) Int. Cl.
*A61K 31/12* (2006.01)
*A23L 1/226* (2006.01)
*C07C 323/22* (2006.01)

(52) U.S. Cl.
CPC ............ *A23L 1/22621* (2013.01); *C07C 323/22* (2013.01)

(58) Field of Classification Search
CPC ..................................................... C07C 323/22
USPC .......................................................... 514/675
See application file for complete search history.

*Primary Examiner* — San-Ming Hui
(74) *Attorney, Agent, or Firm* — XuFan Tseng; Martin Zhang; Elizabeth M. Quirk

(57) ABSTRACT

The present invention is directed to a novel compound, 2-mercapto-5-methyl-4-heptanone, a process of augmenting, enhancing or imparting taste to a material selected from the group consisting of a foodstuff, a chewing gum, a medicinal product, and toothpaste comprising the step of incorporating an olfactory acceptable amount of 2-mercapto-5-methyl-4-heptanone, and a process of improving, enhancing or modifying a fragrance formulation through the addition of an olfactory acceptable amount of 2-mercapto-5-methyl-4-heptanone.

10 Claims, No Drawings

2-MERCAPTO-5-METHYL-4-HEPTANONE AND ITS USE IN FLAVOR AND FRAGRANCE COMPOSITIONS

STATUS OF RELATED APPLICATIONS

This application claims the benefit of U.S. Provisional Application No. 61/737,987, filed Dec. 17, 2012, the contents hereby incorporated by references as if set forth in their entirety.

FIELD OF THE INVENTION

The present invention relates to a new chemical entity and its use as a flavor and fragrance material.

BACKGROUND OF THE INVENTION

There is an ongoing need in the fragrance industry to provide new chemicals to give perfumers and other persons the ability to create new fragrances for perfumes, colognes and personal care products. There is a similar ongoing need for new flavor and aroma compounds such as compounds that provide nutty and fruity sensation. Those with skill in the art appreciate how differences in the chemical structures of the molecules can result in significant differences in the odor, notes and characteristics. For example, small structural differences between close analogs would result in molecules with distinctive flavor properties. These distinctive properties can be highly valuable as they provide unique and distinguished characters to flavor compositions. However, many of these distinctive properties can also be undesirable and, thus, would render molecules not suited for flavor use.

It is well recognized by the art that whether a given molecule possesses useful flavor and fragrance properties and whether its synthesis can be carried out at a large scale to be suitable for commercial application are unpredictable. It requires undue experimentation to develop a particular molecule that meets the criteria of applicability based on the general knowledge in the art. For these reasons, a continuous and extensive effort has been made in the industry to search for novel molecules suitable for flavor and fragrance use that can be produced via an economical process.

SUMMARY OF THE INVENTION

The present invention provides a novel compound, 2-mercapto-5-methyl-4-heptanone, and its use in enhancing (i) the flavor of beverages, foodstuff, chewing gums, dental and oral hygiene products and the like and (ii) the fragrance of perfumes, toilet waters, colognes, personal products and the like. In particular, 2-mercapto-5-methyl-4-heptanone represented by Formula I set forth below is surprisingly found to possess an unexpected, highly desirable, and distinctive hazelnut flavor property:

Formula I

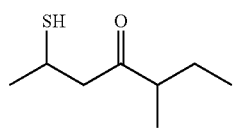

2-Mercapto-5-methyl-4-heptanone possesses fruity and nutty aroma and flavor with an unexpected hazelnut character.

These and other embodiments of the present invention will be apparent by reading the following specification.

DETAILED DESCRIPTION OF THE INVENTION 2-mercapto-5-methyl-4-heptanone of the present invention can be readily prepared from the starting material, 5-methyl-2-hepten-4-one (commercially available at Sigma-Aldrich Inc.), in two steps. The reaction steps can be depicted by a scheme shown as follows:

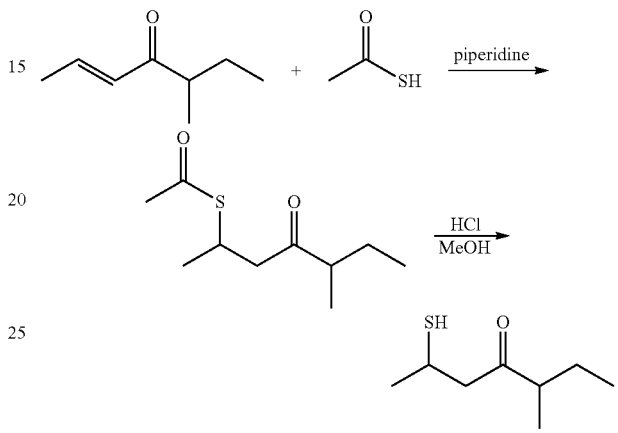

Those with skill in the art will recognize that the compound of the present invention may have a number of isomers including optically active forms. It is intended herein that the compound described herein includes isomeric mixtures as well as specific enantiomers that may be separated using techniques known to those having skill in the art. Suitable techniques include chromatography such as high performance liquid chromatography, referred to as HPLC, and particularly gel chromatography and solid phase microextraction, referred to as SPME.

The compound of the present invention is surprisingly found to possess strong and unexpected flavor effect such as, for example, tropical, fruity, roasted, nutty, meaty, and hazelnut characters, which are demonstrated to be advantageous for its use in augmenting or imparting taste enhancement or somatosensory effect to foodstuff, chewing gums, oral hygiene products, and medicinal products.

The compound of the present invention can also be used in combination with other flavor compounds that are known in the art. When the compound of the present invention is used in an orally consumable composition, it can be combined with conventional flavoring ingredients or adjuvants, which are well known in the art. Requirements of such flavoring ingredients and adjuvants are that: (1) they be organoleptically compatible with the compound of the present invention whereby the flavor of the ultimate consumable composition to which the compound is added is not detrimentally affected by the use of such flavoring ingredients and adjuvants; and (2) they be ingestible acceptable and thus nontoxic or otherwise non-deleterious. In addition, the orally consumable composition can broadly include other flavor materials, vehicles, stabilizers, thickeners, surface active agents, conditioners, and flavor intensifiers.

The use of the compound of the present invention is also widely applicable in current perfumery products, including perfumes, colognes, personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

When used in a fragrance formulation, the compound of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in *Perfumes, Cosmetics and Soaps,* Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein, foodstuff includes both solid and liquid ingestible materials for man or animals, which materials usually do, but need not, have nutritional value. Thus, foodstuff includes food products, such as meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

As used herein, the term "augmenting" in the phrase "augmenting, enhancing or imparting taste to a material" means raising the flavor formulation to a more desirable character. The term "enhancing" means making the flavor formulation greater in effectiveness or providing the flavor formulation with an improved character. The term "imparting" means providing the flavor formulation with a change in character.

As used herein, the term "improving" in the phrase "improving, enhancing or modifying a fragrance formulation" means raising the fragrance formulation to a more desirable character. The term "enhancing" means making the fragrance formulation greater in effectiveness or providing the fragrance formulation with an improved character. The term "modifying" means providing the fragrance formulation with a change in character.

As used herein, an olfactory effective amount is understood to mean the amount of the compound in a flavor or fragrance composition contributes to its particular olfactory characteristics, but the flavor, taste and aroma effect on the overall composition will be the sum of the effect of each flavor or fragrance ingredient. Thus the compound of the present invention can be used to alter the characteristics of a flavor or fragrance composition, or by modifying the flavor, taste and aroma reaction contributed by another ingredient in the composition. The amount will vary depending on many factors including other ingredients, their relative amounts and the effect that is desired.

The usage level of the compound of the present invention varies depending on the product in which the compound is employed. Generally, the level of the compound employed in a product is greater than about 0.5 part per billion by weight, preferably from about 1 part per billion to about 1 part per million by weight, more preferably from about 5 parts per billion to about 500 parts per billion by weight.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to be parts per million, ppb is understood to be parts per billion, L is understood to be liter, mL is understood to be milliliter, g is understood to be gram, mol is understood to be mole, M is understood to be mole per liter, and mmHg is understood to be millimeters (mm) of mercury (Hg).

EXAMPLE I

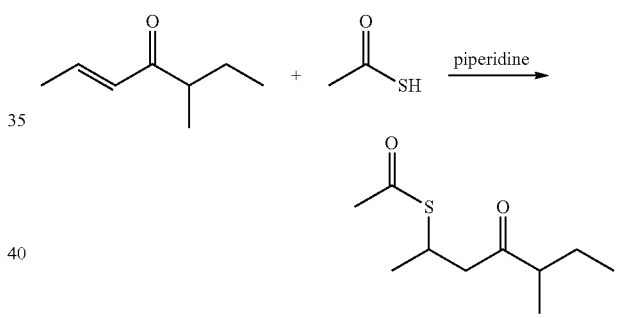

Preparation of S-(5-methyl-4-oxoheptan-2-yl) ethanethioate: A reaction flask was charged with 5-methyl-2-hepten-4-one (200 g, 1.59 mol) and piperidine (6.6 g), and cooled to 15° C. using a cooling bath. Thioacetic acid (241 g, 3.17 mol) was subsequently added to the reaction flask dropwise through an addition funnel The feeding was exothermic. The reaction temperature was kept below 25° C. After the addition was completed, the cooling bath was removed while the reaction was stirred for another hour at room temperature. The reaction mixture was then transferred into a separatory funnel. The organic layer was washed with sodium bicarbonate solution (10%, 250 mL) followed by brine (250 mL), and dried with magnesium sulfate. Further distillation of the obtained crude product under a vacuum (at 78° C. with a pressure of 11.0 mmHg) provided S-(5-methyl-4-oxoheptan-2-yl) ethanethioate (288.0 g) (about 90% yield with a purity over 97% monitored with gas chromatography).

$^1$H NMR (500 MHz) (Chloroform-d): 3.93 ppm (sextet, 1H, J=6.98 Hz), 2.80-2.87 ppm (m, 1H), 2.66 ppm (m, 1H), 2.42 ppm (sextet, 1H, J=6.78 Hz), 2.29 ppm (s, 3H), 1.68 ppm (m, 1H), 1.38 ppm (septet, 1H, J=7.09 Hz), 1.32 ppm (d, 3H, J=6.95 Hz), 1.06 ppm (d, 3H, J=6.88 Hz, of d, J=1.58 Hz), 0.88 ppm (t, 3H, J=7.40 Hz, of d, J=1.50 Hz).

EXAMPLE II

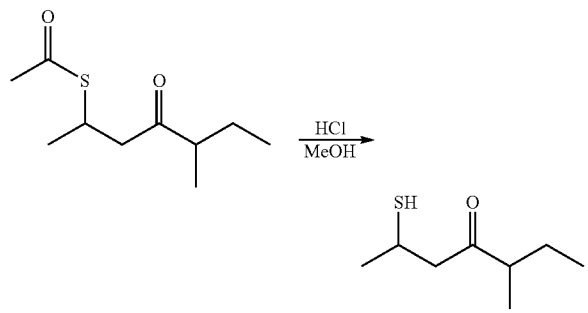

Preparation of 2-mercapto-5-methyl-heptan-4-one: A reaction flask was charged with HCl (1.25 M, 500 mL) in methanol (0.63 mol). S-(5-methyl-4-oxoheptan-2-yl) ethanethioate (127.0 g, 0.63 mol) (synthesized as above in EXAMPLE I) then added into the reaction flask in one portion. The reaction mixture was stirred at 40° C. for about 48 hours, then cooled down to room temperature, and transferred into a separatory funnel Water (250 mL) was added. The reaction mixture was then extracted twice with ethyl acetate (250 mL each time). The organic phases were combined, washed with water (250 mL) followed by brine (100 mL), and then dried with magnesium sulfate. Further distillation of the obtained crude product under a vacuum (at 57° C. with a pressure of 1.33 mmHg) provided 2-mercapto-5-methyl-heptan-4-one (76.0 g) (about 76% yield with a purity over 98% monitored with gas chromatography).

$^1$H NMR (500 MHz) (Chloroform-d): 3.44 ppm (septet, 1H, J=6.70 Hz), 2.72-2.82 ppm (m, 1H), 2.65-2.72 ppm (m, 1H), 2.42 ppm (sextet, 1H, J=6.85 Hz), 1.82-1.85 ppm (m, 1H), 1.69 ppm (m, 1H), 1.39 ppm (m, 1H), 1.33 ppm (d, 3H, J=6.83 Hz, of d, J=2.08 Hz), 1.07 ppm (d, 3H, J=6.93 Hz, of d, J=3.48 Hz), 0.89 ppm (t, 3H, J=7.30 Hz, of d, J=5.63 Hz).

EXAMPLE III

Samples containing 2-mercapto-5-methyl-heptan-4-one were prepared and evaluated as follows. 2-Mercapto-5-methyl-heptan-4-one was demonstrated to possess unexpected and advantageous flavor properties:

| Samples Containing 2-Mercapto-5-methyl-heptan-4-one | Profiles |
|---|---|
| 0.01% in ethanol | Aroma of gassy, tropical, grapefruit, muscat grape, grapes on the vine |
| 20 ppb in water | Flavor of mushroom, meaty, roasted, nutty, toasted, and hazelnut |
| 20 ppb in sugar water (5%) | Flavor of hazelnut, hazelnut flesh, oily, and muscat grape |
| 20 ppb in sugar-acid water (a mixture of sucrose (5%) and citric acid (0.01%)) | Flavor of tropical fruits (grapefruit, papaya, guava, blackcurrant), peach, and concord grape |
| 20 ppb in salt water (0.3%) | Flavor of hazelnut, foxy-grape skin, muscat grape, beefy, smoky, roasted, nutty, toasted, slightly green, and oily |

EXAMPLE IV

Gummy flavor formulas were prepared as follows and tested. 2-Mercapto-5-methyl-heptan-4-one was demonstrated to impart fruity and nutty notes to the formula.

A first mixture of sugar (191.25 g), pectin (11.50 g), water (35.00 g) and high-fructose corn syrup (HFCS) (190.40 g) was prepared and heated to 180° F. A second mixture of gelatin (32.50 g), water (38.65 g), and citric acid (0.25 g) was prepared and added to the first mixture. Various amounts of 2-mrcapto-5-methyl-heptan-4-one were then added and the resulted mixtures were poured into molds. Gummy samples containing 2-mercapto-5-methyl-heptan-4-one at different levels were obtained and evaluated. The results are as follows:

At 20 ppb, 2-mercapto-5-methyl-heptan-4-one provided additional fruity, dark berry, blueberry, and grape notes;

at 50 ppb, 2-mercapto-5-methyl-heptan-4-one provided additional blackcurrant, sulfury, slightly rubber tire, and mushroom notes; and at 100 ppb, 2-mercapto-5-methyl-heptan-4-one provided additional sulfurous note.

What is claimed is:

1. A compound, 2-mercapto-5-methyl-4-heptanone.
2. A composition comprising an olfactory effective amount of 2-mercapto-5-methyl-4-heptanone.
3. The composition of claim 2 further comprising a material selected from the group consisting of foodstuff, a chewing gum, a dental or oral hygiene product, and a medicinal product.
4. The composition of claim 2, wherein the olfactory effective amount is greater than about 0.5 parts per billion by weight.
5. The composition of claim 2, wherein the olfactory effective amount is from about 1 part per billion to about 1 part per million by weight.
6. The composition of claim 2, wherein the olfactory effective amount is from about 5 parts per billion to about 500 parts per billion by weight.
7. A process of augmenting, enhancing or imparting a taste to a material selected from the group consisting of foodstuff, a chewing gum, a dental or oral hygiene product, and a medicinal product comprising the step of incorporating a composition comprising an olfactory effective amount of 2-mercapto-5-methyl-4-heptanone.
8. The process of claim 7, wherein the olfactory effective amount is greater than about 0.5 parts per billion by weight.
9. The process of claim 7, wherein the olfactory effective amount is from about 1 part per billion to about 1 part per million by weight.

10. The process of claim 7, wherein the olfactory effective amount is from about 5 parts per billion to about 500 parts per billion by weight.

* * * * *